US012778412B2

(12) United States Patent
Pichereau et al.

(10) Patent No.: US 12,778,412 B2
(45) Date of Patent: Nov. 3, 2026

(54) METHOD FOR EVALUATING AN INDIVIDUAL'S ASTIGMATISM

(71) Applicant: SIVIEW, Paris (FR)

(72) Inventors: Laure Pichereau, Marcoussis (FR); Kelly Woog, Chevry-Cossigny (FR)

(73) Assignee: SIVIEW, Paris (FR)

( * ) Notice: Subject to any disclaimer, the term of this patent is extended or adjusted under 35 U.S.C. 154(b) by 229 days.

(21) Appl. No.: 18/846,566

(22) PCT Filed: Mar. 13, 2023

(86) PCT No.: PCT/EP2023/056367
§ 371 (c)(1),
(2) Date: Sep. 12, 2024

(87) PCT Pub. No.: WO2023/174883
PCT Pub. Date: Sep. 21, 2023

(65) Prior Publication Data
US 2026/0256351 A1 Sep. 3, 2026

(30) Foreign Application Priority Data
Mar. 14, 2022 (FR) ....................................... 2202201

(51) Int. Cl.
*A61B 3/036* (2006.01)
*A61B 3/00* (2006.01)
(Continued)

(52) U.S. Cl.
CPC ............ *A61B 3/036* (2013.01); *A61B 3/0025* (2013.01); *A61B 3/0285* (2013.01); *A61B 3/032* (2013.01)

(58) Field of Classification Search
CPC ..... A61B 3/036; A61B 3/0025; A61B 3/0285; A61B 3/032
(Continued)

(56) References Cited

U.S. PATENT DOCUMENTS 9,492,074 B1 * 11/2016 Lee ........................ A61B 3/036
2021/0100446 A1 * 4/2021 Pichereau ............ A61B 3/0033
(Continued)

FOREIGN PATENT DOCUMENTS

FR 3 050 922 A1 11/2017
FR 3 078 246 A1 8/2019
(Continued)

OTHER PUBLICATIONS

International Search Report as issued in International Patent Application No. PCT/EP2023/056367, dated May 22, 2023.
(Continued)

*Primary Examiner* — Bumsuk Won
*Assistant Examiner* — Seth D Moser
(74) *Attorney, Agent, or Firm* — CUSHMAN PARTNERS LLC

(57) ABSTRACT

A method for evaluating an individual's astigmatism, the method being carried out subsequently to an evaluation of the visual acuity of an eye of the individual and to a determination of a sphere value for the eye of the individual, the method being carried out based on a prior optical correction for the individual including a prescribed cylinder value and a prescribed axis value for the eye of the individual.

11 Claims, 2 Drawing Sheets

(51) Int. Cl.
*A61B 3/028* (2006.01)
*A61B 3/032* (2006.01)

(58) Field of Classification Search
USPC .................................. 351/235, 239, 241, 246
See application file for complete search history.

(56) References Cited

U.S. PATENT DOCUMENTS

| | | | | |
|---|---|---|---|---|
| 2023/0139007 | A1 * | 5/2023 | Marin | G06N 3/09<br>351/222 |
| 2024/0148245 | A1 * | 5/2024 | Trumm | A61B 3/028 |

FOREIGN PATENT DOCUMENTS

| | | | |
|---|---|---|---|
| FR | 3 097 422 | A1 | 12/2020 |
| WO | WO 2018/031001 | A1 | 2/2018 |
| WO | WO 2018/096140 | A1 | 5/2018 |

OTHER PUBLICATIONS

Allary, J.C., "Methode du Brouillard" in Chapter 5-9, Sep. 2012 Opto-Com edition of the book *Cours d'Optométrie*, 5 pages.

* cited by examiner

METHOD FOR EVALUATING AN INDIVIDUAL'S ASTIGMATISM

CROSS-REFERENCE TO RELATED APPLICATIONS

This application is the U.S. National Stage of PCT/EP2023/056367, filed Mar. 13, 2023 which in turn claims priority to French patent application number 2202201 filed Mar. 14, 2022. The content of these applications are incorporated herein by reference in their entireties.

TECHNICAL FIELD OF THE INVENTION

The technical field of the invention is that of eye examination methods and more particularly that of methods for evaluating astigmatism.

The present invention relates to a method for evaluating an individual's astigmatism and in particular to a method for evaluating an individual's astigmatism based on a previous optical correction. The present invention also relates to a system, a computer program product and a recording medium enabling implementation of the method according to the invention.

TECHNOLOGICAL BACKGROUND OF THE INVENTION

An eye examination is generally carried out on an individual to determine whether he or she needs correction, and if necessary, the type of correction. The correction is then typically provided by a pair of glasses or contact lenses obtained from an optician.

Because of the limited time that practitioners are able to devote to carrying out an eye examination, it has been noticed that 8 to 15% of corrections prescribed in France are not ultimately adapted to the individual's eyesight. Of the individuals prescribed an unsuitable correction, 10% return to their practitioner and then to their optician to obtain a new pair of glasses or contact lenses, which results in significant costs and wasted time.

Among the values prescribed in a correction, the astigmatism value is often the one responsible for an incorrect prescription. Indeed, an eye examination may reveal slight tensional astigmatisms which should not be prescribed, at the risk of aggravating other factors, such as myopia or visual discomfort.

There is therefore a need to check astigmatism value of a prescribed correction in a reduced time, before manufacturing the corresponding pair of glasses or contact lenses.

SUMMARY OF THE INVENTION

The invention offers a solution to the problems discussed previously, by making it possible to evaluate, in a reduced time, an individual's astigmatism from a previously prescribed correction.

A first aspect of the invention relates to a method for evaluating an astigmatism value of an individual's eye implemented subsequently to evaluating visual acuity of the individual's eye and determining a sphere value for the individual's eye, the sphere value determined being non-zero, the method being carried out from a previous optical correction of the individual including a prescribed cylinder value and a prescribed axis value for the individual's eye, the method comprising:

Placing at least one optotype at a fixed distance from the individual's eyes;

Placing, between the individual's eye and the optotype, an initial lens having a value equal to the determined sphere value.

If the prescribed cylinder value is zero:

- If the visual acuity evaluated is greater than or equal to a first predefined visual acuity threshold:
  - Placing, between the individual's eye and the initial lens, a first cylinder having a minimum value along a first axis having a minimum value;
  - Receiving information relating to an improvement in vision for the individual resulting from placing the first cylinder compared with an absence of the first cylinder:
    - If the information received does not reflect an improvement with the first cylinder, assigning an astigmatism value comprising a zero cylinder value to the individual's eye;
    - If the information received reflects an improvement with the first cylinder, removing the first cylinder and determining a cylinder value using a twirling cross-cylinder test starting from the value of the first cylinder and the value of the first axis:
      - If the cylinder value determined is greater than the first cylinder value, determining an axis value via a twirling cross-cylinder test starting from the cylinder value determined and the first axis value and assigning an astigmatism value comprising the cylinder value determined and the axis value determined to the individual's eye;
      - Otherwise, assigning an astigmatism value comprising the cylinder value determined and the first axis value to the individual's eye;
- If the visual acuity evaluated is below a first predefined visual acuity threshold:
  - Placing, between the individual's eye and the initial lens, a second cylinder along a second axis, then along a third axis, then along a fourth axis, then along a fifth axis, the value of the second cylinder depending on the visual acuity evaluated;
  - Receiving information relating to an improvement in vision for the individual resulting from placing the second cylinder for one of the axes from among the second axis, the third axis, the fourth axis and the fifth axis;
    - If the information reflects an improvement in vision for one of the axes, referred to as the preferred axis, from among the second axis, the third axis, the fourth axis and the fifth axis, removing the second cylinder, determining an axis value by means of a twirling cross-cylinder test starting from the value of the second cylinder and the value of the preferred axis, determining a cylinder value via a twirling cross-cylinder test starting from the second cylinder value and the axis value determined and assigning an astigmatism value comprising the cylinder value determined and the axis value determined to the individual's eye;
    - Otherwise, assigning an astigmatism value comprising a zero cylinder value to the individual's eye;

If the prescribed cylinder value is non-zero:

Placing, between the individual's eye and the optotype, an initial cylinder with a value equal to the prescribed cylinder value according to the prescribed axis value;

If the prescribed axis value is between a first axis value and a second axis value or between a third axis value and a fourth axis value, or if the prescribed cylinder value is less than a first cylinder value and the prescribed axis value is between a fifth axis value and a sixth axis value, and the visual acuity evaluated is greater than or equal to a second predefined visual acuity threshold, determining a cylinder value via a twirling cross-cylinder test starting from the prescribed cylinder value and the prescribed axis value and assigning an astigmatism value comprising the cylinder value determined and the prescribed axis value;

If the prescribed cylinder value is between a second cylinder value and a third cylinder value and the prescribed axis value is between a seventh axis value and an eighth axis value:

Placing, between the individual's eye and the initial lens, a first lens with a value equal to the spherical equivalent of the prescribed cylinder value;

Removing the first lens and placing, between the individual's eye and the initial lens, a third cylinder equal in value to the prescribed cylinder value according to the prescribed axis value;

Receiving information relating to an improvement in vision for the individual resulting from placing the third cylinder in relation to the first lens If the information does not reflect an improvement in vision for the individual with the third cylinder in relation to the first lens, assigning an astigmatism value comprising a zero cylinder value to the individual's eye;

Otherwise, removing the third cylinder, determining an axis value via a twirling cross-cylinder test starting from the third cylinder value and the prescribed axis value, determining a cylinder value via a twirling cross-cylinder test starting from the third cylinder value and the axis value determined and assigning an astigmatism value comprising the cylinder value determined and the axis value determined to the individual's eye;

Otherwise, determining an axis value via a twirling cross-cylinder test starting from the prescribed cylinder value and the prescribed axis value, determining a cylinder value via a twirling cross-cylinder test starting from the prescribed cylinder value and the axis value determined and assigning an astigmatism value comprising the cylinder value determined and the axis value determined to the individual's eye.

By virtue of the invention, an individual's astigmatism is evaluated as a function of a previously determined visual acuity and from a previously prescribed astigmatism value on the assumption that the prescribed astigmatism value is close to the individual's true astigmatism value.

In the case where the individual has no prescribed astigmatism and the visual acuity determined is good, it is only ensured that there is no horizontal astigmatism since, insofar as the visual acuity is good, a reverse or oblique astigmatism would be synonymous with stress and should therefore not be prescribed. To do this, a first cylinder having a minimum value along a first axis having a minimum value is placed in front of the individual's eyes: if the individual prefers without the first cylinder, it is confirmed that the individual has no astigmatism. Otherwise, a cylinder search around the value of the first cylinder is performed, an axis search around the value of the first axis being performed only if the cylinder value obtained is greater than the value of the first cylinder.

In the case where the individual has no prescribed astigmatism and the visual acuity determined is not good, it is ensured that there is no weak astigmatism in the end by placing a second cylinder with a value related to the visual acuity determined along several axes. If no axis is preferred, it is confirmed that the individual has no astigmatism. Otherwise, an axis search around the value of the preferred axis is performed followed by a cylinder search around the value of the second cylinder.

In the case where the prescribed axis value is close to the horizontal or the prescribed cylinder value is strong and the prescribed axis value is close to the vertical axis, and the visual acuity determined is very good, the prescribed axis value is considered good and only a cylinder search around the prescribed cylinder value is performed.

In the case where the prescribed cylinder value is low and the prescribed axis value is far from the horizontal axis, it is checked that the inverse or oblique astigmatism is not due to fatigue or accommodation by placing a lens corresponding to the spherical equivalent of the prescribed cylinder value, then a third cylinder of a value equal to the prescribed cylinder value according to the prescribed axis value. If the individual prefers the lens, the individual has no astigmatism in the end. Otherwise, an axis search around the prescribed axis value and then a cylinder search around the prescribed cylinder value are performed.

In the other cases, an axis search around the prescribed axis value and then a cylinder search around the prescribed cylinder value are performed.

Using the visual acuity determined and the prescribed astigmatism value makes it possible to accurately evaluate the individual's astigmatism without having to systematically carry out a complete axis search and then a complete cylinder search. The time required is therefore reduced.

Further to the characteristics just discussed in the previous paragraph, the method according to the first aspect of the invention may have one or more additional characteristics from among the following, considered individually or according to any technically possible combinations.

According to one alternative embodiment, the first visual acuity threshold and the second visual acuity threshold depend on a set of criteria including the individual's age.

According to one alternative embodiment compatible with the previous alternative embodiment, the first visual acuity threshold is 10/10 and the second visual acuity threshold is 12/10.

According to one alternative embodiment compatible with the previous alternative embodiments, the first cylinder has a value of −0.25 dioptre and the first axis has a value of 0°.

According to one alternative embodiment compatible with the previous alternative embodiments, the second axis has a value of 0°, the third axis has a value of 90°, the fourth axis has a value of 45°, and the fifth axis has a value of 135°.

According to one alternative embodiment compatible with the previous alternative embodiments, the first axis value is 0°, the second axis value is 10°, the third axis value is 170° and the fourth axis value is 180°, the first cylinder value is −0.5 dioptre, the fifth axis value is 80° and the sixth axis value is 100°.

According to one alternative embodiment compatible with the previous alternative embodiments, the second cylinder value is −0.5 dioptre, the third cylinder value is 0 dioptre, the seventh axis value is 30° and the eighth axis value is 150°.

A second aspect of the invention relates to a method for evaluating respective astigmatism values for two eyes of an individual, wherein, for each eye of the individual, the respective astigmatism value is evaluated according to the above method.

Thus, the above method can advantageously be implemented on one eye, and then on the other eye of the individual, to obtain astigmatism values for both individual's eyes.

A third aspect of the invention relates to a system for evaluating an individual's astigmatism allowing implementation of the method according to the invention, including:

- a screen configured to display at least one optotype at a fixed distance from the individual's eyes and to display at least one suggestion and/or a selection symbol;
- a lens selector configured to place a lens or an optical cylinder in front of the individual's eyes; and
- an input interface configured to receive information relating to an improvement in vision for the individual following displaying the suggestion and/or the selection symbol;
- a storage memory;
- a calculator configured to implement one of the above methods.

Thus, the method according to the invention can be implemented by the individual whose astigmatism is being evaluated or by a practitioner. Indeed, the individual or the practitioner him/her/herself selects, via the selection means, the suggestion and/or the selection symbol displayed on the display means and the calculator takes these selections into account in order to perform the steps of the method in sequence.

Another aspect of the invention relates to a computer program product comprising instructions which, when the program is executed on a computer, cause the same to implement the steps of the method according to the invention.

Another aspect of the invention relates to a computer-readable recording medium comprising instructions which, when executed by a computer, cause the same to implement the steps of the method according to the invention.

The invention and its different applications will be better understood upon reading the following description and upon examining the accompanying figures.

BRIEF DESCRIPTION TO THE FIGURES

The figures are set forth by way of indicating and in no way limiting purposes of the invention.

DETAILED DESCRIPTION

Unless otherwise specified, a same element appearing in different figures has a single reference.

A first aspect of the invention relates to a method for evaluating an individual's astigmatism, i.e. for determining an astigmatism value for each eye of the individual.

The astigmatism value includes a cylinder value and an axis value if the cylinder value is non-zero.

The method according to the invention is performed from a correction previously prescribed to the individual including a prescribed astigmatism value for each eye of the individual, i.e. a prescribed cylinder value and a prescribed axis value for each eye of the individual.

The method according to the invention is implemented subsequently to evaluating the visual acuity of each eye of the individual on the one hand, i.e. subsequently to determining a visual acuity for each eye of the individual, and to determining a sphere value for each eye of the individual on the other hand.

For each eye of the individual, the sphere value is for example determined from the correction previously prescribed to the individual, further comprising a sphere value prescribed for the individual's eye. The sphere value determined for each eye is non-zero.

Figure 1:
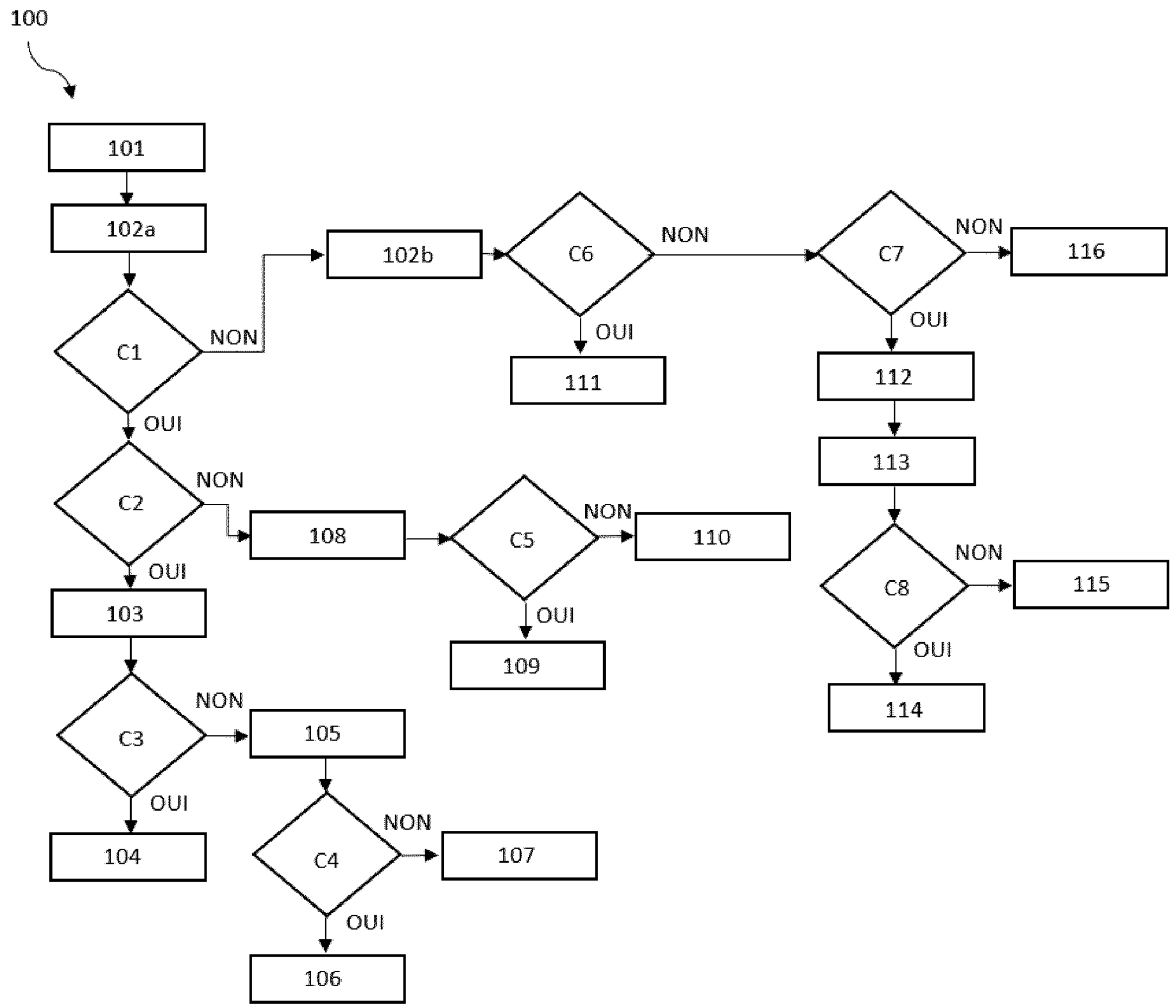
FIG. 1 is a block diagram illustrating the sequence of steps of a method according to the invention.

FIG. 1 is a block diagram illustrating the sequence of steps of the method 100 according to the invention.

The method 100 according to the invention is carried out within the scope of a monocular step of the eye examination, i.e. the steps of the method 100 according to the invention are carried out for one eye of the individual, and then for the other eye of the individual.

The method 100 according to the invention is carried out, for example, for the right eye and then for the left eye of the individual.

A first step 101 of the method 100 according to the invention consists in placing at least one optotype at a fixed distance from the individual's eyes.

By "optotype", it is meant a character or figure used for measuring visual acuity.

The first step 101 consists, for example, in placing at least one group of letters corresponding to an expected minimum acuity in front of the individual's eyes. The minimum expected acuity depends, for example, on the individual's age or corresponds, for example, to an acuity of 10/10.

The optotype is for example placed at least 4 metres from the individual's eyes and preferably at least 5 metres from the individual's eyes.

A second step 102*a* of the method 100 according to the invention consists in placing in front of the individual's eye an initial lens with a value equal to the sphere value determined prior to the implementation of the method 100 according to the invention. The initial lens is then placed between the individual's eye and the optotype.

If a first condition C1 is met, i.e. if the cylinder value prescribed for the individual's eye is zero, it is checked whether a second condition C2 is met.

If the second condition C2 is met, i.e. if the previously visual acuity evaluated for the individual's eye is greater than or equal to a first predefined visual acuity threshold, a third step 103 of the method 100 according to the invention is performed.

The first visual acuity threshold is for example defined as a function of a set of parameters, comprising for example the individual's age.

The first visual acuity threshold is, for example, 10/10.

The third step 103 of the method 100 according to the invention consists in placing a first cylinder having a minimum value in front of the individual's eye and along a first axis having a minimum value. The first cylinder is then placed between the individual's eye and the initial lens.

The first cylinder has, for example, a value of −0.25 dioptre and the first axis has, for example, a value of 0°.

If a third condition C3 is met, i.e. if the individual prefers without the first cylinder rather than with the first cylinder, or if the individual sees no difference between with and without the first cylinder, a fourth step 104 of the method 100 according to the invention is performed.

By "the individual prefers without the first cylinder rather than with the first cylinder", it is meant that the individual experiences less discomfort relative to his/her vision without the first cylinder than with the first cylinder, i.e. that his/her vision seems more comfortable to him/her without the first cylinder. In particular, the individual's preference may be reflected by receiving information, emitted by the individual, relating to an improvement in vision resulting from placing the first cylinder compared with the absence of the first cylinder. When condition C3 is met, the information received does not reflect an improvement with the first cylinder. For example, the information may be received via a selection device (a touch screen or a selection joystick) in which the individual enters his or her preference.

The fourth step 104 of the method 100 according to the invention consists in assigning to the individual's eye, an astigmatism value comprising a zero cylinder value.

If the third condition C3 is not met, i.e. if the individual prefers with the first cylinder rather than without the first cylinder (in other words, the information received reflects an improvement with the first cylinder) a fifth step 105 of the method 100 according to the invention is performed.

The fifth step 105 of the method 100 according to the invention consists in removing the first cylinder from in front of the individual's eye, and then performing a twirling cross-cylinder test starting from the value of the first cylinder and the value of the first axis to determine a cylinder value.

If a fourth condition C4 is met, i.e. if the cylinder value determined in the fifth step 105 is greater than the value of the first cylinder, a sixth step 106 of the method 100 according to the invention is performed.

The sixth step 106 of the method 100 according to the invention consists in performing a twirling cross-cylinder test starting from the cylinder value determined in the fifth step 105 and from the value of the first axis in order to determine an axis value, then in assigning to the individual's eye an astigmatism value comprising the cylinder value determined in the fifth step 105 and the axis value determined in the sixth step 106.

If the fourth condition C4 is not met, i.e. if the cylinder value determined in the fifth step cylinder determined in the fifth step 105 is less than the value of the first cylinder, a seventh step 107 of the method 100 according to the invention is performed.

The seventh step 107 of the method 100 according to the invention consists in assigning to the individual's eye an astigmatism value comprising the cylinder value determined in the fifth step 105 and the value of the first axis.

If the second condition C2 is not met, i.e. if the visual acuity previously evaluated for the individual's eye is less than the first predefined visual acuity threshold, an eighth step 108 of the method 100 according to the invention is performed.

The eighth step 108 of the method 100 according to the invention consists in placing in front of the individual's eye, a second cylinder having a value depending on the visual acuity previously evaluated for the individual's eye. The second cylinder is then placed between the individual's eye and the initial lens.

The value of the second cylinder is determined, for example, from the visual acuity previously evaluated for the individual's eye, according to Table 5-1 in the section Méthode du Brouillard in 5-9, in the September 2012 Opto-Com edition of the book "Cours d'Optométrie" by Jean-Charles Allary.

The second cylinder is first placed along a second axis, then along a third axis, then along a fourth axis, and then along a fifth axis.

The second axis and the fourth axis, the third axis and the fifth axis, and the third axis and the fourth axis, are separated by about 45°, for example.

The second axis has, for example, a value of 0°, the third axis has, for example, a value of 90°, the fourth axis has, for example, a value of 45°, and the fifth axis has, for example, a value of 135°.

If a fifth condition C5 is met, i.e. if the individual prefers one of the second axis, the third axis, the fourth axis and the fifth axis, a ninth step 109 of the method 100 according to the invention is performed. The individual's preference can be expressed by receiving information relating to an improvement in vision for the individual resulting from placing the second cylinder for one of the axes from among the second axis, the third axis, the fourth axis and the fifth axis. Thus, condition C5 is met when said information reflects an improvement in vision for one of the axes, referred to as the preferred axis.

By "the individual prefers one of the axes", it is meant that the individual experiences less discomfort relative to his/her vision when the second cylinder is placed along the preferred axis.

The ninth step 109 of the method 100 according to the invention consists in removing the second cylinder from in front of the individual's eye, then carrying out a twirling cross-cylinder test starting from the value of the second cylinder and the value of the preferred axis in order to determine an axis value, then performing a twirling cross-cylinder test using the second cylinder value and the axis value determined in said ninth step 109 to determine a cylinder value, and then assigning to the individual's eye an astigmatism value comprising the cylinder value determined in said ninth step 109 and the axis value determined in said ninth step 109.

If a fifth condition C5 is not met, i.e. if the individual does not identify a preferred axis among the second axis, the third axis, the fourth axis and the fifth axis, a tenth step 110 of the method 100 according to the invention is performed.

The tenth step 110 of the method 100 according to the invention consists in assigning to the individual's eye an astigmatism value comprising a zero cylinder value.

If the first condition C1 is not met, i.e. if the cylinder value prescribed for the individual's eye is non-zero, the method 100 comprises a step of placing **102*b***, between the individual's eye and the optotype, an initial cylinder (also called a "cylinder lens") with a value equal to the cylinder value prescribed according to the prescribed axis value. The initial cylinder is then placed between the individual's eye and the optotype.

It is then checked whether a sixth condition C6 is met.

If the sixth condition C6 is met, i.e. if the prescribed axis value for the individual's eye is between a first axis value and a second axis value or between a third axis value and a fourth axis value, or if the prescribed cylinder value for the individual's eye is less than a first cylinder value and the prescribed axis value for the individual's eye is between a fifth axis value and a sixth axis value, and the previously visual acuity evaluated for the individual's eye is greater than or equal to a second predefined visual acuity threshold, an eleventh step 111 of the method 100 according to the invention is performed.

The first axis value, the second axis value, the third axis value and the fourth axis value are, for example, axis values close to the horizontal axis.

The first axis value is for example 0°, the second axis value is for example 10°, the third axis value is for example 170° and the fourth axis value is for example 180°.

The first cylinder value is for example a strong cylinder value and the fifth axis value and the sixth axis value are for example values close to the vertical axis.

The first cylinder value is for example −0.5 dioptre, the fifth axis value is for example 80° and the sixth axis value is for example 100°.

The second visual acuity threshold is for example defined as a function of a set of parameters, comprising for example the individual's age.

The second visual acuity threshold is, for example, 12/10.

The eleventh step 111 of the method 100 according to the invention consists in performing a twirling cross-cylinder test starting from the cylinder value prescribed for the individual's eye and the axis value prescribed for the individual's eye in order to determine a cylinder value, then in assigning to the individual's eye an astigmatism value comprising the cylinder value determined during this eleventh step 111 and the axis value prescribed for the individual's eye.

If the sixth condition C6 is not met, i.e. if the axis value prescribed for the individual's eye is not between the first axis value and the second axis value or between the third axis value and the fourth axis value, or if the cylinder value prescribed for the individual's eye is greater than or equal to the first cylinder value or the axis value prescribed for the individual's eye is not between the fifth axis value and the sixth axis value, or the visual acuity evaluated for the individual's eye is less than the second predefined visual acuity threshold, it is checked whether a seventh condition C7 is met.

If the seventh condition C7 is met, i.e. if the cylinder value prescribed for the individual's eye is between a second cylinder value and a third cylinder value, and the axis value prescribed for the individual's eye is between a seventh axis value and an eighth axis value, a twelfth step 112 of the method 100 according to the invention is performed.

The second cylinder value and the third cylinder value are, for example, low or zero cylinder values.

The seventh axis value and the eighth axis value are, for example, oblique axis values, remote from the horizontal axis.

The second cylinder value is for example −0.5 dioptre, the third cylinder value is for example 0 dioptre, the seventh axis value is for example 30° and the eighth axis value is for example 150°.

The twelfth step 112 of the method 100 according to the invention consists in placing in front of the individual's eye a first lens with a value equal to the spherical equivalent of the cylinder value prescribed for the individual's eye. The first lens is then placed between the individual's eye and the initial lens.

A thirteenth step 113 of the method 100 according to the invention consists in removing the first lens from in front of the individual's eye, then in placing according to the axis value prescribed for the individual's eye, a third cylinder having a value equal to the cylinder value prescribed for the individual's eye. The third cylinder is then placed between the individual's eye and the initial lens.

If an eighth condition C8 is met, i.e. if the individual prefers the first lens rather than the third cylinder, a fourteenth step 114 of the method 100 according to the invention is performed. The individual's preference may be reflected by receiving information relating to an improvement in vision for the individual resulting from placing the third cylinder with respect to the first lens. Condition C8 is thus met when the information does not reflect an improvement in vision for the individual with the third cylinder compared to the first lens.

By "the individual prefers the first lens to the third cylinder", it is meant that the individual experiences less discomfort relative to his/her vision with the first lens than with the third cylinder.

The fourteenth step 114 of the method 100 according to the invention consists in assigning to the individual's eye an astigmatism value comprising a zero cylinder value.

If the eighth condition C8 is not met, i.e. if the individual prefers the third cylinder rather than the first lens, a fifteenth step 115 of the method 100 according to the invention is performed.

The fifteenth step 115 of the method 100 according to the invention consists in removing the third cylinder from in front of the individual's eye, then performing a twirling cross-cylinder test starting from the value of the third cylinder and the axis value prescribed for the individual's eye to determine an axis value, then performing a twirling cross-cylinder test using the third cylinder value and the axis value determined in said fifteenth step 115 to determine a cylinder value, and then assigning to the individual's eye an astigmatism value comprising the cylinder value determined in said fifteenth step 115 and the axis value determined in said fifteenth step 115.

If the seventh condition C7 is not met, i.e. if the cylinder value prescribed for the individual's eye is not between the first cylinder value and the second cylinder value or the axis value prescribed for the individual's eye is not between the fifth axis value and the sixth axis value, a sixteenth step 116 of the method 100 according to the invention is performed.

The sixteenth step 116 of the method 100 according to the invention consists in performing a twirling cross-cylinder test starting from the cylinder value prescribed for the individual's eye and the axis value prescribed for the individual's eye in order to determine an axis value, then in carrying out a twirling cross-cylinder test starting from the cylinder value prescribed for the individual's eye and the axis value determined during this sixteenth step 116 in order to determine a cylinder value, then in assigning to the individual's eye an astigmatism value comprising the cylinder value determined in said sixteenth step 116 and the axis value determined in said sixteenth step 116.

A second aspect of the invention relates to a method for evaluating respective astigmatism values for two eyes of an individual, wherein, for each eye of the individual, the respective astigmatism value is evaluated according to the method 100 according to the first aspect of the invention. Thus, the method 100 according to the first aspect of the invention can be implemented on one eye, and then on the other eye of the subject, to obtain astigmatism values for both eyes of the subject.

A third aspect of the invention relates to a system for evaluating an individual's astigmatism allowing the implementation of the method 100 according to the invention by the individual or a third party, for example a practitioner.

Figure 2:
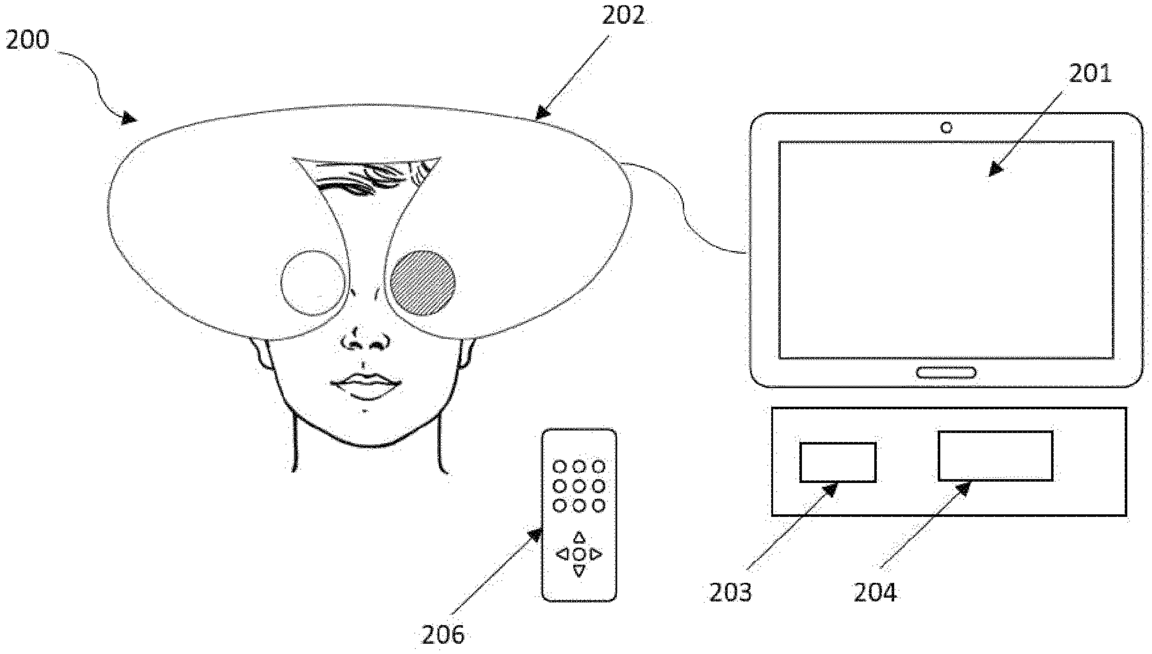
FIG. 2 shows a schematic representation of a system according to the invention.

FIG. 2 shows a schematic representation of the system 200 according to the invention.

The system 200 includes display means configured to display at least one optotype at a fixed distance from the individual's eyes.

The display means are, for example, a screen 201 as illustrated in FIG. 2, or a poster.

According to one embodiment, the display means 201 are also configured to display suggestions and/or validation symbols.

For example, the display means is configured to display a suggestion for validating that a lens, an axis or a cylinder is preferred.

The system 200 then also includes an input interface 206 configured to select a suggestion and/or a symbol.

The input interface 206 is for example a remote controller as illustrated in FIG. 2, a tablet, a console or a microphone.

The system 200 also includes a lens selector 202 configured to place optical lenses or cylinders in front of the individual's eyes.

The lens selector 202 is for example an automatic refractor head as illustrated in FIG. 2.

The system 200 according to the invention includes a storage memory 203 and a calculator 204 configured to manage the display means, the lens selector 202, and the input interface 206 to allow implementation of the steps of the method 100 according to the invention.

For example, following the third step 103 of the method 100, the display means display a first suggestion allowing a choice with the first cylinder, a second suggestion allowing a choice without the first cylinder and a third suggestion for indicating that there is no difference with or without the first cylinder. The individual selects the third suggestion by virtue of the input interface 206, and the calculator 204 processes the selection of the third suggestion to initiate performance of the fourth step 104 of the method 100.

The invention claimed is:

1. A method for evaluating an astigmatism value of an individual's eye implemented subsequently to evaluating visual acuity of the individual's eye and to determining a sphere value for the individual's eye, the sphere value determined being non-zero, the method being performed from a previous optical correction of the individual comprising a prescribed cylinder value and a prescribed axis value for the individual's eye, the method comprising:

placing at least one optotype at a fixed distance from the individual's eyes;

placing, between the individual's eye and the optotype, an initial lens having a value equal to the sphere value determined;

if the prescribed cylinder value is zero:

if the visual acuity evaluated is greater than or equal to a first predefined visual acuity threshold:

placing, between the individual's eye and the initial lens, a first cylinder having a minimum value along a first axis having a minimum value;

receiving information relating to an improvement in vision for the individual resulting from placing the first cylinder compared with an absence of the first cylinder:

if the information received does not reflect an improvement with the first cylinder, assigning an astigmatism value comprising a zero cylinder value to the individual's eye;

if the information received reflects an improvement with the first cylinder, removing the first cylinder and determining a cylinder value via a twirling cross-cylinder test starting from the value of the first cylinder and the value of the first axis:

if the cylinder value determined is greater than the value of the first cylinder, determining an axis value via a twirling cross-cylinder test starting from the cylinder value determined and the value of the first axis and assigning an astigmatism value comprising the cylinder value determined and the axis value determined to the individual's eye;

otherwise, assigning an astigmatism value comprising the cylinder value determined and the first axis value determined to the individual's eye;

if the visual acuity evaluated is less than a first predefined visual acuity threshold:

placing, between the individual's eye and the initial lens, a second cylinder along a second axis, then along a third axis, then along a fourth axis, then along a fifth axis, the value of the second cylinder depending on the visual acuity evaluated;

receiving information relating to an improvement in vision for the individual resulting from placing the second cylinder for one of the axes from among the second axis, the third axis, the fourth axis and the fifth axis;

if the information reflects an improvement in vision for one of the axes, referred to as the preferred axis, from among the second axis, the third axis, the fourth axis and the fifth axis, removing the second cylinder, determining an axis value via a twirling cross-cylinder test starting from the value of the second cylinder and the value of the preferred axis, determining a cylinder value via a twirling cross-cylinder test starting from the second cylinder value and the axis value determined, and assigning an astigmatism value comprising the cylinder value determined and the axis value determined to the individual's eye;

otherwise, assigning an astigmatism value comprising a zero cylinder value to the individual's eye;

if the prescribed cylinder value is non-zero:

placing, between the individual's eye and the optotype, an initial cylinder with a value equal to the prescribed cylinder value according to the prescribed axis value;

if the prescribed axis value is between a first axis value and a second axis value or between a third axis value and a fourth axis value, or if the prescribed cylinder value is less than a first cylinder value and the prescribed axis value is between a fifth axis value and a sixth axis value, and the visual acuity evaluated is greater than or equal to a second predefined visual acuity threshold, determining a cylinder value via a twirling cross-cylinder test starting from the prescribed cylinder value and the prescribed axis value, and assigning an astigmatism value comprising the cylinder value determined and the prescribed axis value;

if the prescribed cylinder value is between a second cylinder value and a third cylinder value and the prescribed axis value is between a seventh axis value and an eighth axis value:

placing, between the individual's eye and the initial lens, a first lens with a value equal to the spherical equivalent of the prescribed cylinder value;

removing the first lens and placing, between the individual's eye and the initial lens, a third cylinder with a value equal to the prescribed cylinder value according to the prescribed axis value;

receiving information relating to an improvement in vision for the individual resulting from placing the third cylinder relative to the first lens:

if the information does not reflect an improvement in vision for the individual with the third cylinder relative to the first lens, assigning an astigmatism value comprising a zero cylinder value to the individual's eye;

otherwise, removing the third cylinder, determining an axis value via a twirling cross-cylinder test starting from the third cylinder value and the prescribed axis value, determining a cylinder value via a twirling cross-cylinder test starting from the third cylinder value and the axis value determined, and assigning an astigmatism value comprising the cylinder value determined and the axis value determined to the individual's eye;

otherwise, determining an axis value via a twirling cross-cylinder test starting from the prescribed cylinder value and the prescribed axis value, determining a cylinder value via a twirling cross-cylinder test starting from the prescribed cylinder value and the axis value determined, and assigning an astigmatism value comprising the cylinder value determined and the axis value determined to the individual's eye.

2. The method according to claim 1, wherein the first visual acuity threshold and the second visual acuity threshold are dependent on a set of criteria, including the individual's age.

3. The method according to claim 1, wherein the first visual acuity threshold is 10/10 and the second visual acuity threshold is 12/10.

4. The method according to claim 1, wherein the first cylinder has a value of −0.25 dioptre and the first axis has a value of 0°.

5. The method according to claim 1, wherein the second axis has a value of 0°, the third axis has a value of 90°, the fourth axis has a value of 45°, and the fifth axis has a value of 135°.

6. The method according to claim 1, wherein the first axis value is 0°, the second axis value is 10°, the third axis value is 170° and the fourth axis value is 180°, the first cylinder value is −0.5 dioptre, the fifth axis value is 80° and the sixth axis value is 100°.

7. The method according to claim 1, wherein the second cylinder value is −0.5 dioptre, the third cylinder value is 0 dioptre, the seventh axis value is 30° and the eighth axis value is 150°.

8. A method for evaluating respective astigmatism values for two eyes of an individual wherein, for each eye of the individual, the respective astigmatism value is evaluated according to claim 1.

9. A system for evaluating an individual's astigmatism allowing automatic implementation of the method according to claim 1, comprising:

a screen configured to display at least one optotype at a fixed distance from the individual's eyes and to display at least one suggestion and/or a selection symbol;

a lens selector configured to place a lens or an optical cylinder in front of the individual's eyes; and an input interface configured to receive information relating to an improvement in vision for the individual following displaying the suggestion and/or the selection symbol;

a storage memory, and a calculator configured to implement the method according to claim 1.

10. A computer program product comprising instructions which, when the program is executed on a computer, cause the same to implement the steps of the method according to claim 1.

11. A non-transitory computer-readable recording medium comprising instructions which, when executed by a computer, cause the same to implement the steps of the method according to claim 1.

* * * * *